United States Patent
Bumm

(10) Patent No.: US 7,146,216 B2
(45) Date of Patent: Dec. 5, 2006

(54) IMPLANTABLE MUSCLE STIMULATION DEVICE FOR TREATING GASTRO-INTESTINAL REFLUX DISEASE

(75) Inventor: Rudolf Bumm, Munich (DE)

(73) Assignee: Pulsion Medical Systems AG, Munich (DE)

( * ) Notice: Subject to any disclaimer, the term of this patent is extended or adjusted under 35 U.S.C. 154(b) by 749 days.

(21) Appl. No.: 10/289,215

(22) Filed: Nov. 7, 2002

(65) Prior Publication Data

US 2003/0120321 A1 Jun. 26, 2003

(30) Foreign Application Priority Data

Nov. 9, 2001 (DE) ................. 101 55 087

(51) Int. Cl.
*A61N 1/36* (2006.01)
(52) U.S. Cl. .................. 607/40; 607/62; 600/593
(58) Field of Classification Search ............... 607/40, 607/2, 59, 62, 72, 133; 600/593, 547
See application file for complete search history.

(56) References Cited

U.S. PATENT DOCUMENTS

| | | | |
|---|---|---|---|
| 5,188,104 A | | 2/1993 | Wernicke et al. |
| 6,535,764 B1 | * | 3/2003 | Imran et al. .......... 607/40 |
| 6,591,137 B1 | * | 7/2003 | Fischell et al. ........ 607/40 |

FOREIGN PATENT DOCUMENTS

| | | |
|---|---|---|
| EP | 1 004 330 A1 | 5/2000 |
| WO | WO 02/38217 A2 | 5/2002 |

OTHER PUBLICATIONS

European Search Report Dated Dec. 17, 2003.

* cited by examiner

*Primary Examiner*—Kennedy Schaetzle
(74) *Attorney, Agent, or Firm*—Nixon Peabody LLP; Donald R. Studebaker

(57) ABSTRACT

A muscle stimulation device has a control unit (1) that determines frequency and/or intensity of electrical impulses in dependence upon the degree of stomach filling. The impulses function to stimulate lower esophageal sphincter (11) by means of stimulating electrodes (5a, 5b, 5c) disposed radially around the sphincter (11). A computer program, executable by means of a microprocessor (10), is installed in the control unit, the program designed such that a higher stomach filling degree causes a stronger stimulation of the sphincter (11) or its substitute. The sphincter reacts to the stimulation by exerting a corresponding pressure onto a lower esophagus area (12). An increased risk of gastric reflux as a consequence of the patient's substantial food ingestion is countered by an increased stimulation of the sphincter, which in turn causes an elevated closing pressure at the lower esophagus (12). When the stomach is empty or nearly empty, the closing pressure is correspondingly reduced and the food ingestion is facilitated.

11 Claims, 1 Drawing Sheet

Figure 1:
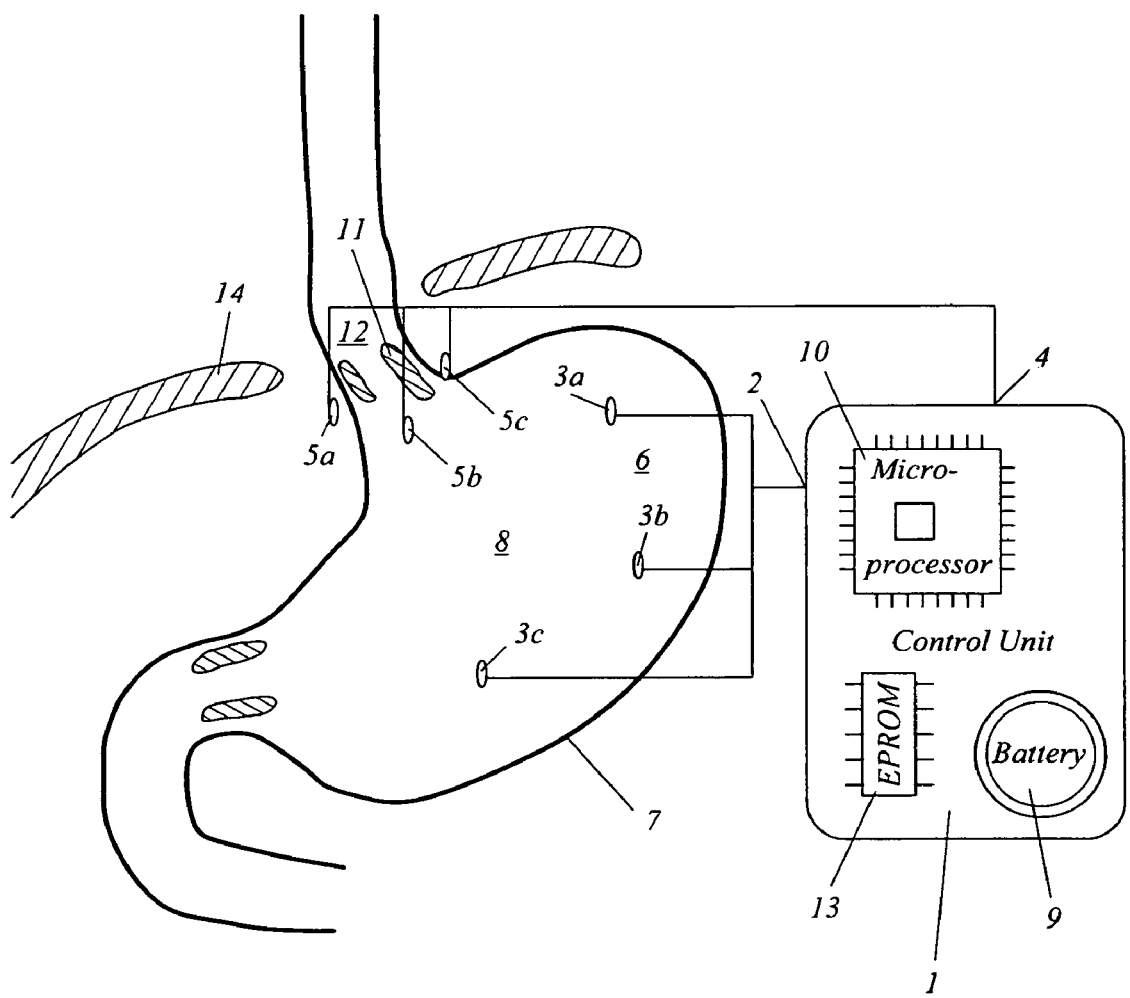

IMPLANTABLE MUSCLE STIMULATION DEVICE FOR TREATING GASTRO-INTESTINAL REFLUX DISEASE

The present invention relates to an implantable muscle stimulator for treating gastro-esophageal reflux disease (GERD).

Gastro-esophageal reflux disease is the most common ailment of the upper gastrointestinal tract. The factor at its root is insufficiency of the lower esophageal sphincter in preventing the backward transit (reflux) of gastric contents, so-called stomach juice, and in more severe cases, also of duodenal secretions with pancreas and gall enzymes, into the esophagus (gullet). Moreover, in many patients, the angle of entry of the esophagus into the stomach (the angle of His) is flattened. A so-called hiatal hernia (crural membrane hernia) also occurs in many cases. The latter amounts to a shift of the stomach inlet above the membrane, which aggravates GERD even more. Prolonged gastro-esophageal reflux can lead to esophagitis, up to the point where squamous epithelium in the esophagus becomes replaced with columnar epithelium.

In the so-called Barrett's esophagus phase, which is usually considered the last stage of a prolonged GERD, there is a frequent occurrence of adenocarcinomas, tumors of the distal esophagus. These are now among the most frequently diagnosed types of tumors in the western civilization.

Gastro-esophageal reflux disease can be treated with medications inhibiting the secretion of gastric acid. While the treatment is usually effective in healing esophagitis, recurrence is common when the medication is stopped, and lifelong medication therapy is thus needed. This is obviously expensive and cumbersome for GERD patients. Moreover, inhibiting the secretion of the gastric acid does not prevent the reflux of gall and pancreatic enzymes into the esophagus. There is no known drug therapy that is proven effective without the necessity for continuing application.

A typical, commonly used, surgical treatment of GERD is known as fundoplication. During the fundoplication surgery, the upper curve of the stomach (the fundus) is wrapped around the esophagus and sewn into place to form a "cuff" around the end portion of the esophagus in the area of the lower esophageal sphincter (LES). After fundoplication, many patients experience difficulty controlling burping and vomiting. Occasionally, increased gas and flatulence is experienced. If the cuff is too tight, frequent problems occur with swallowing and passing food to the stomach, which occasionally may even necessitate another surgical procedure. If the cuff is too loose, the gastro-esophageal reflux is likely to reoccur (a reflux relapse). The GERD reoccurrence is also common if the cuff becomes loose in time. In such case, drug therapy or another surgical procedure can be applied. If the cuff becomes dislocated, the anti-reflux mechanism usually overreacts (so-called hypercompetence) and the resulting pain and difficulty swallowing often make another surgery inevitable.

U.S. Pat. No. 5,716,385 issued to University of Virginia discloses an implantable crural diaphragm pacemaker and a method of using such pacemaker for treating GERD. The pacemaker senses electromyography signals indicative of intermittent relaxations of the lower esophageal sphincter and responds by electrical stimulation of the muscles of the crural diaphragm. This raises the pressure in the lower esophagus area. However, this approach sometimes only reduces the reflux disease rather than eliminate it entirely.

U.S. Pat. No. 6,097,984 issued to Medtronic, Inc. discloses an implantable muscle stimulation device of the above-discussed type, for stimulating the lower esophageal sphincter (LES) in dependence upon esophageal motility. The stimulator is programmed such that a reading of high esophageal motility results in a reduction of LES stimulation, whereby the closing pressure of the sphincter (sphinctereal pressure) is reduced allowing food or liquid to pass from the esophagus through to the stomach. A reading of low esophageal motility boosts the stimulation of the lower esophageal sphincter, giving rise to a higher LES closing pressure.

However, this control routine can bring about serious problems. For one thing, swallowing movements with concomitant increased esophageal motility can occur even without food intake. Thus, swallowing can temporarily trigger relaxation of the sphincter so that involuntary swallowing during sleep can trigger a nightly reflux, particularly dreaded by GERD patients. Even gum chewing after a meal can seriously interfere with sphincter stimulation routine controlled by esophageal motility. Secondly, esophageal motility in GERD patients is highly disturbed anyway. Such disturbed esophageal motility can in turn give rise to a prolonged high LES closing pressure and to dysphagia (swallowing disorders) due to the principal control setting of the device.

Furthermore, sensing of esophageal motility by means of implantable electrodes is technically difficult to realize. Particularly, it can hardly be determined from a detected esophageal wave, or at least not reliably, whether any food bolus whatsoever is present or whether merely saliva was swallowed, and this uncertainty leads to the above-mentioned problems.

It should be noted that the installation of the device of U.S. Pat. No. 6,097,984 requires a two-opening surgery. Aside from the surgical opening to the lower esophageal sphincter to install the pacemaker, another surgical entry must also be made to fix the esophagus sensors. This is done through an additional pulmonar endoscopy or through an opening in the diaphragm. These procedures, particularly the latter, can bring about the risk of additional complications in GERD patients. Generally, placement of sensors on esophagus cannot be considered harmless.

It is an object of the present invention to provide a device that is effective in counteracting gastro-esophageal reflux and which would allow to eliminate conventional medicinal or surgical therapies with their associated problems as discussed above.

It is another object of the invention to provide a computer program for control and adjustment of such device.

In accordance with one aspect of the invention, there is provided an implantable muscle stimulation device which comprises:

a. at least two implantable electrodes for stimulating the sphincter or its substitute,
 b. at least one implantable sensor for generating signals indicative of the degree of filling of patient's stomach, and
 c. a control unit which comprises an impulse transmitter for sending electrical impulses to the stimulating electrodes and a signal input for receiving sensor signals.

The frequency and/or the intensity of the electrical impulses can be controlled as a function of the sensor signal, and preferably in such a manner that a higher degree of patient's stomach filling effects a stronger stimulation of the sphincter (or its substitute) and thus a higher sphinctereal pressure. Thus, when the stomach is full and the risk of gastric reflux is correspondingly high, the device causes a higher closing pressure of the sphincter (or its substitute) on the esophagus, while when the stomach is empty or barely filled, the pressure is reduced allowing easy food ingestion. In contrast to the prior art, there is no risk of prolonged high closing pressure of the lower esophageal sphincter. The dependence of sphincter stimulation upon the stomach filling level eliminates also the undesired consequences of swallowing reflexes without food ingestion.

In contrast to the prior art, it is an advantage of the device of the invention that it can be installed without the need for two surgical incisions. The sensor system can be attached to the stomach wall and the stimulation electrodes can be attached to the lower esophageal sphincter through one surgical opening, when performing a laparoscopy.

In a preferred embodiment of the invention, the sensor may be a dilation receptor which is preferably provided with at least one strain gauge.

In another particularly preferred alternative embodiment of the invention, the sensor comprises at least two, preferably three to five electrodes for measuring electric impedance of gastric tissues.

Preferably, the control unit comprises at least one battery. It is recommended to select a long-lasting battery type with a satisfactory storable energy density, e.g. a lithium cell battery.

In a preferred embodiment of the invention, the control unit is provided with at least one integrated circuit and/or a microprocessor. This allows for a higher degree of miniaturization and thus improves the patient's comfort.

In another embodiment of the invention, the device of the invention comprises three to five stimulation electrodes.

It is particularly advantageous to provide the control unit additionally with a control input through which the frequency and/or the intensity of the electrical impulses is controllable via an external signal. This provision makes it possible to enable the patient, for instance after consuming a substantial meal, to set the device in a simple manner to maximum sphincter stimulation. The control input can also be used for calibration.

According to another aspect of the invention, there is provided a computer program comprising executable instructions for controlling the frequency and/or intensity of electrical impulses to stimulate a patient's sphincter (LES) or sphincter substitute, in response to signals from an implanted sensor, the signals indicating the stomach's filling level. Preferably, the computer program is designed, i.e. has a control characteristic, such that a fuller stomach corresponds to a more vigorous stimulation of the sphincter or sphincter substitute and thus to a higher sphinctereal pressure.

According to yet another aspect of the invention, there is provided a method for treating gastro-esophageal reflux disease. The method includes the steps of receiving a signal from an implantable sensor, the signal being indicative of a degree of patient's stomach filling; and stimulating a sphincter or its substitute in dependence upon the signal from the implantable sensor by controlling at least one of a frequency and an intensity of electrical impulses. Therein a higher stomach filling degree causes a stimulation of the sphincter or its substitute with electrical impulses having at least one of the frequency and the intensity increased in dependence upon an increasing stomach filling degree.

An embodiment of the invention is described below in more detail with reference to a schematic drawing, not to scale. FIG. 1 illustrates a basic design of a muscle stimulation device of the invention, in implanted condition.

The muscle stimulation device shown in FIG. 1 has a control unit 1 with an input 2 to which are connected sensor electrodes 3a, 3b, 3c, and with an output 4 which is connected to stimulation electrodes 5a, 5b, 5c. The sensor electrodes 3a, 3b, 3c are implanted in the area of the greater stomach curvature 6 to measure continuously the impedance of the gastric wall 7. The impedance readings enable the control unit 1 to determine the level to which the stomach 8 is filled.

The control unit 1 has a replaceable lithium battery 9 as an electrical voltage source, and is also provided with a microprocessor 10 and an integrated control circuits (not illustrated). The unit 1 serves to determine the frequency and intensity of electrical impulses in dependence upon the stomach filling level. The purpose of the impulses, as explained already, is the direct stimulation of the sphincter (lower esophageal sphincter) 11 by means of stimulation electrodes 5a, 5b, 5c which are placed radially around the sphincter 11.

For performing this control function, the control unit 1 is provided with a computer program that can be implemented by means of a microprocessor 10 and is designed such that a higher stomach filling degree, or level, corresponds to a stronger stimulation of the sphincter 11 or sphincter substitute. The sphincter 11 reacts to the stimulation by exerting a corresponding pressure upon the region of the lower esophagus 12. When the risk of gastric reflux increases due to the patient's substantial food ingestion, this is counteracted by a corresponding stimulation of the sphincter 11 which raises the sphinctereal pressure at the lower esophagus 12. On the contrary, when the stomach 8 is less full, a correspondingly lower sphinctereal pressure facilitates food ingestion. The computer program can be stored for example on an EPROM chip 13 in the control unit.

The control unit 1 can be calibrated externally via an external wireless signal input (not illustrated), so that for example suitable physiological upper limits can be set for the maximum stimulation current that must be supplied to the electrodes. For this purpose, the computer program has an appropriate calibration routine. In addition, the stimulation of the sphincter 11, and thus the sphinctereal pressure at the lower esophagus 12, can be set manually to a maximum value via the external wireless signal input.

The stimulation electrodes 5a, 5b, 5c as well as the sensor electrodes 3a, 3b, 3c can be implanted for example by means of laparoscopy. Ideally, the control unit 1 is inserted in a pouch of tissue under the patient's costal arch, in the fashion of a conventional heart pacemaker.

If the sphincter 12 cannot be sufficiently stimulated, a sphincter substitute cuff can be produced by preparing a pedicle flap from the patient's own tissue, for example muscle tissue of the diaphragm 14.

The invention claimed is:

1. An implantable muscle stimulation device for treating gastro-esophageal reflux disease, the device comprising:
  a) at least two implantable electrodes for stimulating a patient's sphincter or its substitute,
  b) at least one implantable sensor for generating a signal indicative of the degree of the patient's stomach filling, and
  c) a control unit comprising an impulse transmitter for supplying electrical impulses to the stimulating electrodes and a signal input for receiving signals from the sensor,
  wherein at least one of a frequency and an intensity of the electrical impulses are controllable in dependence upon the sensor signal such that a higher degree of stomach filling causes a stronger stimulation of the sphincter and consequently a higher sphincter closing pressure.

2. The implantable device according to claim 1, wherein the sensor is a dilation receptor.

3. The implantable device according to claim 1, wherein the sensor comprises at least two measuring electrodes for measuring an impedance of a patient's stomach tissue.

4. The implantable device according to claim 3, wherein the sensor comprises between three to five measuring electrodes for measuring the impedance of the stomach wall.

5. The implantable muscle stimulation device according to claim 1, wherein the control unit comprises at least one battery.

6. The implantable device according to claim 5, wherein the control unit comprises at least one integrated control circuit.

7. The implantable device according to claim 6, wherein the control unit comprises at least one microprocessor.

8. The implantable device according to claim 7, wherein the control unit further comprises a control input for controlling and/or calibrating at least one of the frequency and the itnensity of the electrical impulses by means of an external signal.

9. A implantable device according to claim 1, comprising between three to five stimulation electrodes.

10. A storage medium having data stored therein, the data comprising executable instructions for executing the steps of:

controlling at least one of a frequency and an intensity of electrical impulses; and, stimulating a sphincter or its substitute in dependence upon said signal from an implantable sensor, the signal indicative of a degree of patient's stomach filling wherein a higher stomach filing degree causes a stimulation of the sphinchter or its substitute with electrical impulses having at least one of the frequency and the intensity increased in dependence upon an increasing stomach filling degree.

11. A method for treating gastro-esophageal reflux disease, said method including the steps of receiving a signal from an implantable sensor, the signal indicative of a degree of patient's stomach filling; and, stimulating a sphincter or its substitute in dependence upon said signal from said implantable sensor by controlling at least one of a frequency and an intensity of electrical impulses, wherein a higher stomach filling degree causes a stimulation of the sphincter or its substitute with electrical impulses having at least one of the frequency and the intensity increased in dependence upon an increasing stomach filling degree.

* * * * *